United States Patent [19]
Raskin et al.

[11] Patent Number: 6,159,270
[45] Date of Patent: *Dec. 12, 2000

[54] PHYTOREMEDIATION OF METALS

[75] Inventors: Ilya Raskin, Manalapan; Nanda P. B. A. Kumar, New Brunswick; Slavik Douchenkov, East Brunswick, all of N.J.

[73] Assignee: Edenspace Systems Corporation, Reston, Va.

[ * ] Notice: This patent is subject to a terminal disclaimer.

[21] Appl. No.: 09/040,755

[22] Filed: Mar. 18, 1998

Related U.S. Application Data

[63] Continuation of application No. 08/252,234, Jun. 1, 1994, Pat. No. 5,785,735, which is a continuation-in-part of application No. 08/073,258, Jun. 4, 1993, Pat. No. 5,364,451.

[51] Int. Cl.⁷ ............................................... C22B 3/24
[52] U.S. Cl. ......................... 75/711; 75/712; 210/602
[58] Field of Search ....................... 75/711, 712; 210/602

[56] References Cited

U.S. PATENT DOCUMENTS

| | | | |
|---|---|---|---|
| 5,364,451 | 11/1994 | Raskin et al. | 75/710 |
| 5,785,735 | 7/1998 | Raskin et al. | 75/711 |

*Primary Examiner*—Melvyn Andrews
*Attorney, Agent, or Firm*—Brenda Herschbach Jarrell; Choate, Hall & Stewart

[57] ABSTRACT

A process for removal of metal ions from soil and methods for effecting such removal are described. The process is based on manipulating the growth of crop and crop-related members of the plant family Brassicaceae in metal-containing soils so that the metal in the soils is made more available to the plants. These particular plants will absorb metals into their roots making the metals non-leachable from the soils or will absorb the metal into their roots and transfer them to the shoots and/or roots which can be easily harvested.

9 Claims, 2 Drawing Sheets

PHYTOREMEDIATION OF METALS

The present application is a continuation of application U.S. Ser. No. 08/252,234, filed Jun. 1, 1994, now U.S. Pat. No. 5,785,735. Which is in turn a continuation-in-part of U.S. Ser. No. 08/073,258, filed Jun. 4, 1993 now U.S. Pat. No. 5,364,451. The entire contents of both of these related applications are incorporated herein by reference.

The invention was made with U.S. government support under Grant No. R818619-01-0 awarded by the U.S. Environmental Protection Agency to Rutgers, the State University of New Jersey. The government has certain rights in the invention.

BACKGROUND OF THE INVENTION

Deposition of metal-rich mine tailings, metal smelting, leather tanning, electroplating, emissions from gas exhausts, energy and fuel production, downwash from powerlines, intensive agriculture and sludge dumping are the most important human activities which contaminate soil systems with large amounts of toxic metals. The list of sites contaminated with toxic metals grows larger every year, presenting a serious health problem and a formidable danger to the environment. In spite of the growing number of metal-contaminated soil sites, the costly process of removing and burying metal-contaminated soils, or isolating the contaminated sites, remain the most commonly used methods for reclaiming metal-contaminated soils.

SUMMARY OF THE INVENTION

The present invention pertains to a method of removing an amount of metal from a metal-containing soil environment using plants of the family Brassicaceae. In order to accomplish this, at least one member of the family Brassicaceae is contacted with the metal-containing soil environment and the metal-containing soil environment is manipulated in a manner sufficient to increase availability of metal within the metal-containing soil environment to the member of the plant family Brassicaceae. The plant member is maintained in the metal-containing soil environment under conditions of increased metal availability for a time and under conditions sufficient for the member to accumulate an amount of metal from the metal-containing soil environment.

In one embodiment, the step of manipulating includes tilling the soil to a depth greater than about 15 cm so that metal-containing soil is brought into contact with the root zone of the Brassicaceae. Preferably, the soil is tilled to a depth of about 50 cm.

In another embodiment, the soil is excavated to depths greater than about 20 cm and placed in elevated seed beds or hills. The Brassicaceae member is planted directly on the excavated soil in the hills and, when fully grown, the roots are harvested.

Another embodiment entails adding a chelating agent to the soil in an amount sufficient to form a soluble or insoluble complex with at least one divalent metal in the soil. Further, an electric field may be applied to the soil to increase metal mobility. The methods also include decreasing pH of the metal-containing soil to at least pH 5.5 or less by adding an effective amount of an organic or inorganic acid such as, for example, nitric acid, hydrochloric acid, sulfuric acid, acetic acid, and citric acid. Further manipulative methods include addition of a compound to the soil that will be metabolized by the roots and/or associated bacteria (collectively called the "rhizosphere") with concomitant production of protons, leading to a decrease in soil pH.

Further methods of the invention include foliar fertilization of the Brassicaceae with a phosphate fertilizer, preferably at a rate of about 10–18 kg/hectare. Other methods include harvesting the Brassicaceae member from the metal-containing soil environment before seeds of the Brassicaceae mature and harvesting roots of the Brassicaceae member.

Preferred plants used in the present methods are crop members and crop-related members of the family Brassicaceae selected for an ability to accumulate at least 10 times more metal in shoots on a dry weight basis that the amount of metal present in the metal-containing soil. Selected plant members are also able to accumulate at least 20 times more metal in roots on a dry weight basis that the amount of metal present in the metal-containing soil. Preferred crop members are selected from the group consisting of *Brassica juncea* and *Brassica carinata*. Preferred crop-related members are selected from the group consisting of *Raphanus sativus* (L.) (radish), *Sinapis alba* (L.) (white mustard), *S. arvensis* (L.), *S. flexuosa* Poiret and *S. pubescens* (L.).

Metals accumulated by these methods include lead, chromium, cadmium, nickel, and zinc.

BRIEF DESCRIPTION OF THE DRAWINGS

FIG. 1 is a bar graph illustrating accumulation of lead by *Brassica juncea* cultivars in shoots (FIG. 1A) and roots (FIG. 1B).

DETAILED DESCRIPTION OF THE INVENTION

One aspect of the present invention is a method for removing metals from metal-contaminated soil using metal-accumulating plants of the family Brassicaceae. This is accomplished by manipulating the soil environment in a way that increases availability of metal to the plant. The manipulations described herein (See Example 1) are generally designed to maximize metal uptake by plants, something that would be considered antithetical to current practices and counterproductive by conventional agronomists. Specifically, manipulating the soil environment according to the invention and then growing one more members of these Brassicaceae under conditions sufficient for the plants to accumulate metal in their biomass is generally contrary to current agricultural practices for growing crop and crop-related Brassicas. See texts describing conventional practices, such as for example, Chopra, V. L. and Prakash, S., (eds.) *Oilseed Brassicas in Indian Agriculture*, Vikas Publishing House Ltd., New Delhi, (1991); Downey, R. K. and Robbelen, G., "Brassica species", pp. 339–362 in Robbellen et al. (eds.), *Oil Crops of the World*, McGraw-Hill, New York , 1989, incorporated herein by reference.

In brief, preferred methods of the invention involve soil and /or plant manipulations that impact on crop establishment and tillage, soil acidity and soil fertility. The Brassicaceae manipulated in this manner may include genetically altered plants, as described herein. In this context, metal "accumulating" plants refers to the ability of the plants described herein to perform one, or more, of the following activities: (i) transporting metal from soil particles and/or soil liquid into roots; (ii) physical and/or chemical sorption of metal to the root biomass; (iii) prevention or inhibition of leaching of the metal from the soil environment. The term "increases availability of metal" refers to the ability of the present methods to render metals in soils more amenable to plant root uptake than they would be absent the present methods.

The preferred plants used in the present method are members of the plant family Brassicaceae. The most preferred members of this family belong to the tribe Brassiceae. Members of this tribe include mustards of the genus Brassica and related species, described in more detail below.

A key aspect of the present invention is that the preferred method relies upon use of crop and/or crop-related members of the above-identified family and tribe. The term "crop member" refers specifically to species of the genus Brassica which are commercially grown as sources for primarily two different types of products: (i) vegetables, forage, fodder and condiments; and (ii) oilseeds. Examples of "vegetative" crop members of the family Brassicaceae include, but are not limited to, digenomic tetraploids such as *Brassica juncea* (L.) Czern. (mustard), *B. carinata* Braun (ethopian mustard), and monogenomic diploids such as *B. oleracea* (L.) (cole crops), *B. nigra* (L.) Koch (black mustard), *B. campestris* (L.) (turnip rape) and *Raphanus sativus* (L.) (radish). Examples of "oil-seed" crop members of the family Brassicaceae include, but are not limited to, *B. napus* (L.) (rapeseed), *B. campestris* (L.), *B. juncea* (L.) Czern. and *B. tournifortii* and *Sinapis alba* (L.) (white mustard).

"Crop-related" members are those plants which have potential value as a crop and as donors of agronomically useful genes to crop members. Thus, crop-related members are able to exchange genetic material with crop members, thus permitting breeders and biotechnologists to perform interspecific (i.e., from one species to another) and intergeneric (i.e., from one genus to another) gene transfer. Those having ordinary skill in the art will understand that methods of exchanging genetic material between plants and testing effects of interspecific and intergeneric gene transfer are well characterized. See, for example Goodman et al., Science, 236: 48–54, 1987, incorporated herein by reference.

"Crop-related" members include members of species belonging, but not limited to, genera of Sinapsis, Thlaspi, Alyssum, and Eruca. "Crop-related" members not presently identified, or suspected of removing metal, can be identified using the screening methods described herein. Unless indicated otherwise, "crop and/or crop-related" members will be referred to collectively as "members".

The plant members used in the present methods include mutagenized and/or genetically engineered plants (i.e, interspecific and/or intergeneric hybrids). For example, ethylmethylsulfonate (EMS) is a potent mutagen which increases genetic variability by increasing the frequency of genomic mutations. See, for example, Redei, G. P. "Genetic Manipulations of Higher Plants", L. Ledoux (ed), Plenum Press, N.Y, 1975. Ethylmethylsulfonate has been used in selection programs to produce heritable changes in plant biochemistry and physiology, particularly in *Arabidopsis thaliana*, a member of the Brassicaceae.

In sum, the members used in the present invention are plants that: (a) can be grown to high biomass; (b) are adaptable for growth in various agroclimatic conditions; (c) are adaptable to modified, non-conventional agricultural practices, described herein, for monoculture; (d) are amenable to genetic manipulation by mutagenesis and/or gene transfer; (e) can produce several crops per year; and (f) are related to known wild plants which do accumulate metals.

Preferred plant members used in the present invention should be contrasted to "wild" or non-crop and/or non-crop-related members; i.e., those species that are endemic to metal-containing soils in scattered areas of the world. These wild members are not amenable to large scale agricultural practices and they normally have very low rates of germination and biomass accumulation in the laboratory and in the field.

Examples of non-crop-related members of the family Brassicaceae are members of the genus Alyssum found on serpentine soils in southern Europe and Thiaspi from calamine soils throughout Europe. In particular, non-crop-related members of this family include *T. caerulescens* Whitesike Mine, *A. tenium, A. lesbiacum, A. murale* and *T. ochroleucum* (see also Baker, et al., Biorecovery 1:81–126 (1989); Reeves and Brooks, Environ. Poll., 31: 277 (1983); Baker et al., Taxon, 34: 89 (1985)).

In one embodiment of the method, a screening system (described in Example 2) is used to identify terrestrial plant species with the highest metal accumulating potential (i.e. metal content of dried plant residue/metal content of growth medium). The seeds of these self-pollinating lines are then subjected to EMS mutagenesis using, for example, the methods of Estell et al, "The mutants of Arabidopsis", p. 89 in *Trends in Genetics*, Elsevier Science Publishers, B.V., Amsterdam, 1986. (See Example 3). Briefly, mutagenesis is accomplished by soaking dry seeds in EMS solution at room temperature. The EMS induces heterozygous mutations in those cells which will produce the reproductive structures. The M1 generation of plants is allowed to self-fertilize and at least 50,000 seedlings of the M2 progeny are screened for metal tolerance in artificial aqueous solutions containing various metal concentrations. The most tolerant M2 plants, those growing most vigorously, are analyzed for accumulation of metals.

The terrestrial plants used in the methods of the present invention can be genetically manipulated using well-established techniques for gene transfer. It is well-known that a variety of non-photosynthetic organisms respond to metals by production of metallothioneins (MT's), low molecular weight proteins encoded by structural genes. See, for example G. Maroni, "Animal Metallothioneins," pp. 215–232 in *Heavy Metal Tolerance in Plants: Evolutionary Aspects*, (ed. A. J. Shaw), CRC Press, Inc., Florida, (1990). The present invention contemplates increasing root uptake of metals by heterologous expression of MT's in transgenic plants.

In another embodiment of the method, a mammalian MT cDNA (e.g. monkey) can be obtained commercially or from an established source and a restriction enzyme fragment cloned into, for example, an Agrobacterium-based plant transformation/expression vector such as pJB90, a derivative of pGSFR780A. See, De Block et al, *Physiol. Plant.* 91: 694–701 (1989).

Seedling segments of terrestrial plants used in the present method are then incubated in the presence of a suspension of bacterial cells (e.g. *Agrobacterium tumefacieus*) carrying the expression vector. After several days, the regenerating seedling segments are transferred to the appropriate selection medium and further incubated. This results in transformants containing the mammalian MT genome (see Example 6).

The transformants are analyzed for the presence of MT DNA by Southern and Northern hybridization using mammalian MT as the probe. The transformants are also analyzed for expression of MT protein by immunoblot analysis with antisera against the mammalian MT. See established protocols of, for example, Sambrook et al. (1989) Molecular Cloning: A Laboratory Manual, Cold Spring Harbor Laboratory Press, N.Y, incorporated herein by reference.

Sexual and asexual (i.e., somatic) hybridization is another way of introducing metal-accumulating traits into members of the Brassicaceae. Hybridization has been used to transfer agronomically important traits from related species to crop brassicas. See, for example, Salisbury and Kadkol, "Genetics," *Life Sci. Adv.* 8: 65–87 (1989).

The term "metal" preferably refers to metal ions that are found in the metal containing environment. It will be appreciated that this term will also include elemental metal that is not in an ionic form. The metals that can be accumulated according to the method of the present invention include stable metals and radioactive metals such as lead, chromium, mercury, cadmium, cobalt, barium, nickel, molybdenum, copper, arsenic, selenium, zinc, antimony, beryllium, gold, manganese, silver, thallium, tin, rubidium, vanadium, strontium, yttrium, technecium, ruthenium, palladium, indium, cesium, uranium, plutonium, and cerium. The term "metal" is also intended to include more than one metal since plants may concentrate several different metals (See Example 7), implying that the mechanism of metal uptake is not always metal specific. The term "metal" also includes mixtures of metals and common organic pollutants such as, for example, lead or chromium in combination with nitrophenol, benzene, alkyl benzyl sulfonates (detergents), polychlorinated biphenyls (PCB's) and/or halogenated hydrocarbons (e.e., trichloroethylene).

The metal-containing environment into which these plants are introduced is not intended to limit the scope of the invention. That is, as long as the environment can sustain growth of members of the family Brassicaceae, the metal-containing environment includes a wide range of soil environments of varying degrees of water saturation, organic matter content, mineral content, and the like. It will be appreciated by those of ordinary skill in the art that the term "soil" can, therefore, include a wide variety of chemical and physical types.

The metal-accumulating members suitable for the present methods will extract metal from the environment into the roots of the plant. The plants may translocate the metals from the roots into the shoots (i.e., the above ground portions of the plant). The rates of accumulation of metal can vary depending on a variety of factors, including the ratio of soluble and insoluble metal in the soil, the total metal concentration, soil type, pH, moisture content, organic matter content, soil temperature, planting density, and fertilizer use.

Generally, metal accumulation by the preferred members of the family Brassicaceae can be as high as 1000-fold above levels present in the soil. Preferred plant members accumulate several percent of metal as dry weight of shoot biomass and up to 30% metal by weight in dried root biomass. Particularly preferred are those plants selected for their ability to accumulate at least 10 times more metal in shoots on a dry weight basis than the metal present in the metal-containing soil and/or at least 20 times more metal in roots on a dry weight basis than the metal present in the metal-containing soil. Shoots are routinely harvested for certain Brassica species, for example *B. campestris, B. juncea* and *B. oleracea*, but roots are not routinely harvested, especially for most oil-seed Brassicaceae.

The members of the family Brassicaceae of the present invention have undergone screening and selection procedures to yield several lines of fast growing metal-accumulating plants that can effectively remove radioactive and non-radioactive metals from artifactual and natural soils. These plants concentrate metals in roots and transport the metals to the above-ground shoots which can be easily harvested.

The screening procedures detailed in Example 2 can be applied to other members of the family Brassicaceae and other metal ions that are not described here. To measure metal accumulation of any plant in a metal-containing soil, seeds of the particular plant(s) to be tested are grown in a greenhouse, the appropriate metal is administered to the plant and soil, and the roots and shoots harvested for routine determination of biomass and metal content. Chemical analysis of metal content in soils and plants is well-characterized. See, for example, Blincoe et al., *Comm. Soil. Plant Anal.*, 18: 687 (1987); Baker, D. E. and Suhr, S. H., "Atomic Absorption Spectrometry", pp. 13–27 in *Methods of Soil Analysis*, part 2, Am. Soc. Agron., Madison, Wis., (1982). Metal in plant tissues is preferably assayed with plasma spectrometry, following ashing and acid extraction. Metal remaining in the solution is measured by, for example, atomic absorption or plasma spectrometry. See, Soltanpour et al., "Optical emission spectrometry", pp. 29–65 in *Methods of Soil Analysis*, part 2, Am. Soc. Agron., Madison, Wis., (1982).

The invention described herein will be illustrated by the following examples.

EXAMPLE 1

Growing and Harvesting Practices

The present Brassica growing methods include practices suitable for increasing the amount of metal accumulated by the plant; practices very different from those used to grow Brassicas for food, fodder or oils.

A. Soil Preparation Methods

Conventional agronomic practices for Brassicas involve soil tilling down to a maximum depth of about 5–8 cm (2–3 inches) in India and 10–13 cm (4–5 inches) in Canada. See, for example, "Canola and Rapeseed: Production, Chemistry, Nutrition, and Processing Technology", ed. M. Shahidi, Van Nostrand Reinhold, New York, 1990, and Canola Growers Manual, Canada Council of Canada, 1984, p. 703, both of which are incorporated herein by reference. Experiments have shown that tillage below 15–18 cm (6–7 inches) is of little value. In contrast, present methods of the invention involve tilling soil in a manner that purposely exposes the Brassicaceae root zone to maximum amounts of metal-contaminated soil. This is accomplished by tilling the soil to depths greater than 2 cm and as far down as 50 cm. Conventional implements may be employed for this purpose, provided that they are suitable for tilling down to the depths required by the present methods. These implements include moldboard plows, chisel plows, tandem and offset disc plows, and various harrowers known to those having ordinary skill in the art. The exact implement used will depend on factors such as soil moisture, soil texture, weed cover and the like.

B. Soil Treatments to Increase Metal Availability to Plants

Metal uptake by plants is considered highly undesirable because metal contaminated plants are toxic to humans or animals. Nevertheless, the ability of crop and crop-related Brassicaceae to accumulate meal in shoots and roots is directly related to metal availability in soils. The present metal-remediating plants are therefore used in combination with soil treatments or amendments which make metals in soils more available to the roots of the plants.

In one embodiment, one or more metal chelating agents are added to the soil in amounts sufficient to increase metal mobility but not sufficient to affect plant growth and development (i.e., an "effective" amount). Determination of effective amounts of chelating agent may be made by measuring the effects of soil amendments of chelator on soil metal mobility. Soluble metals are extracted from soil by equilibrating about 5g of soil with about 25 ml of 0.01 M calcium nitrate (to maintain ionic strength) for about 2 hours on a mechanical shaker. After the equilibration period, the suspension is centrifuged (between 3000–5000×g) for about 15 minutes to separate the solution from the soil. The supernatant solution is then analyzed for the desired water-soluble metal concentration. See, for example, Mench et al., *J. Environ. Qual.* 23: 58–63 (1994). Measured metal concentration is correlated with the various soil amendments to optimize conditions in order to maximize metal solubility in the soil and maximize plant availability.

The amount of chelating agent, and the time of administration of the chelating agent will vary, being primarily a function of the amount of metal in the soil and soil type. Many chelating agents will form soluble or partially coluble complexes with metal ions which can make the metal more available to the plants and allow Brassicaceae to accumulate a particular metal. Exemplary metal chelating agents of this are given in Dawson et al., (eds), "Stability Constants of Metal Complexes", pp. 399–415 in Data for Biochemical Research, Claredon Press, Oxford, UK, 1986, incorporated herein by reference and include ammonium purpurate (murexide), 2,3-butane-dione dioxime (dimethylglyoxime), 3,6 disulfo-1,8-dihydroxynaphthalene (chromotroic acid), and thiourea, alpha-benzoin oxime (cupron), trans-1,2-diaminocyclohexanetetraacetic acid (CDTA), diethylenetriaminopentaacetic acid (DTPA), 2,3-dimercapto-1-propanol, diphenylthiocarbazone, nitrilotriacetic acid (NTA), substituted 1,10-phenanthrolines (e.g., 5-nitro-1,10 phenanthroline), sodium deithyldithiocarbamate (cupral), 2-thenoyl-2-furoylmethane, thenoyl-trifluoroacetone, triethylenetetramine, and ethylenediaminetetraacetic acid (EDTA) and citric acid. Other chelating agents may form insoluble complexes with metals and serve to: (i) concentrate metals so they may be physically or chemically accumulated (i.e., sorbed) onto roots of the plants; and/ or (ii) prevent leaching or other removal of metals from the vicinity of the root zone.

Chelating agents are preferably applied to the soil by conventional irrigation pipes or other ground level irrigation systems. Chelating agents may also be applied through other commercially available fertilizer and chemical application equipment, including large volume sprayers. Chelating agents may be applied through broadcast methods for large areas or banding methods for the root zone. Chelating agents are preferably applied at concentrations from 0.1–10 mmol/ kg soil at volumes ranging from about 5 to 200 tons per acre.

Further treatments are designed to increase metal mobility in the soil by decreasing soil pH. Conventional methods of growing Brassicaceae generally require soil in the pH range 5.8–6.2 for optimum production and the available literature suggests that soils with lower pH be specifically amended with base (e.g., lime) prior to seeding to increase the pH. See, "Agronomy of Canola in the United States", pp. 25–35 in Canola and Rapeseed, Production,Chemistry, Nutrition, and Processing Technology, (ed. F. Shahidi), Van Nostrand Reinhold, New York, 1990, incorporated herein by reference.

In preferred methods of the present invention, pH of the metal-contaminated soil is dropped to about pH 4.5–5.5 by acidifying soil with effective amounts of organic or inorganic acids such as nitric acid, hydrochloric acid, sulfuric acid, acetic acid and citric acids. Acids are preferably applied to the soil by conventional irrigation pipes or other ground level irrigation systems. However, acids may also be applied through other commercially available fertilizer and chemical application equipment, including large volume sprayers. Acids may be applied preferably at concentrations from 0.1 mM to 1.0 M at volumes ranging from about 5 to 200 tons per acre or at levels sufficient to drop soil pH in the plant rhizosphere (down to about 40 cm) to between 4.5 and 5.5 pH units.

Further, compounds may be added to the soil that depress soil pH because of biological activity of roots and microorganisms. Examples of these compounds include urea or ammonium sulfate. This so-called "biological acidification" occurs because the positively charged ammonium ions that are incorporated into the roots and/or microorganisms are replaced with positively charged protons exuded or otherwise released from the rhizosphere into the soil, thus lowering the soil pH. The ammonium-containing compounds are applied at 0.5 to about 2.0 tons per acre. Yields of Brassicaceae will be reduced at pH levels below about 5.5 but the present methods require a balance between reduction in growth potential due to increased soil acidity and increase in availability of metals in metal-contaminated soils due to lowered pH. Most preferably, the methods described herein weigh this balance in favor of increasing metal availability so that the Brassicaceae will accumulate the metal.

Metal uptake may be further enhanced by using electrical fields to increase metal mobility. See Probstein and Hicks, *Science* 260: 498–503 (1993), incorporated herein by reference. In these general methods, a direct current electric field is applied across electrode pairs placed in the ground. The electric field induces motion of liquids and dissolved ions.

Metal availability may be further enhanced by rapidly dropping soil pH by at least 2 pH units over a period of several days by adding strong chelators or acids prior to harvest but after the plants have reached the harvestable stage. This treatment is designed to decrease soil pH to between 3–4.5. Acids are preferably applied to the soil by conventional irrigation pipes or other ground level irrigation systems or other commercially available fertilizer and chemical application equipment, including large volume sprayers. Acids are preferably applied in amounts sufficient to drop soil pH below 4.5 and concentrations may range from 0.2 mM to 0.2 M at volumes ranging from about 5 to 200 tons per acre. Chelates are applied at levels that cause visible phytotoxicity and growth retardation in plants. Although such harsh treatment may slow or arrest plant growth or even kill the plants, higher levels of metal accumulation in roots and shoots is expected before the plants stop growing and/or die. In addition, the harvesting of already killed plants is easier since less weight needs to be handled.

C. Foliar Fertilization

Commonly used practices for Brassica cultivation involve use of nitrogen/phosphorous/potassium fertilizers broadcast into the soil. See, for example, "Canola Growers Manual", Canola Council of Canada 1984, and Yusuf and Bullock, *J. Plant Nutrition*, 12: 1279–1288, 1993, incorporated herein by reference. Addition of phosphates to the soil leads to formation of insoluble complexes with heavy metals and is counterproductive in the present context since phosphate addition reduces the availability of heavy metals to plants and decreases efficiency of metal remediation.

To prevent addition of phosphate to soils while maintaining adequate plant nutrition, crop and crop-related Brassicas are foliar fertilized with, for example, ammonium phosphate. Foliar fertilization refers to the spraying of nutrient solutions to the foliage in which the nutrients are absorbed into the plant through the leaves. For macronutrients such as nitrogen and phosphorous, the quantities that can be absorbed are too small to be of much use in large-scale commercial agronomic practices. See "Canola Growers Manual", id. Nevertheless, for purposes of soil metal remediation, foliar addition of phosphate, and soil addition of nitrogen, will reduce addition of phosphates directly to soil while maintaining adequate plant nutrition. Brassicaceae grown for metal accumulation are sprayed with a foliar fertilizer having a high phosphorous content (e.e., non-ammonium phosphate at a rate of 10–18 kg/hectare). Foliar fertilizers may be applied via conventional pesticide sprayers.

D. Harvesting Before Seed Maturation

Conventionally, oil-seed brassicas are grown to maturity and the seeds are harvested. See Shahidi, supra. In contrast, oilseed plants used in the present methods are harvested at the vegetative state, before the seeds mature. The exact harvest time is determined by selecting a plant age which provides maximum metal removal capacity from unit surface area.

E. Harvesting only Shoots and Roots

Conventionally, oil-seed brassicas are grown for their seeds and vegative brassicas are grown for their leaves or stems. Thus, for highest yields of Brassicaceae, particularly the oil-seeds, the plants need to be swathed, i.e., removed above the ground level, exactly like cereal crops. Conventional swathers and combines are used in these procedures. Nevertheless, much of the metal taken up by oil-seed and vegetative brassicas is concentrated in the roots (See also Examples 5 and 6). Therefore, methods of the invention involve harvesting roots, either manually or by adapting conventional agricultural machinery used for beet, carrot or potato harvesting. Metal-containing soil at depths greater than about 20 cm may be excavated and filed into hills alongside the furrows. Brassicaceae are grown directly on the excavated hills. Although this is conventional technology for root crops such as carrots, beets, and potatoes, Brassicaceae are not normally grown in this manner. Nevertheless, the roots of Brassicaceae, especially the oilseed brassicas, may be easily harvested from the hills by undercutting the roots with a blade or plough.

EXAMPLE 2

Screening Assay

The seeds of crop and/or crop-related species of selected members of the Brassicaceae are sown in a potting mix (Terralite™ Metro-Mix™; mfg. by Grace Fiera Horticultural Products Co., Milpetas, Calif.) and grown in a greenhouse equipped with supplementary lighting (16 h photoperiods; 24° C.). Seedlings are fertilized every two days with a full strength Hoagland's solution. After 10 days the seedlings are transplanted (two per 3.5 inch plastic pot) into an acid pre-washed 1:1 (v/v) mixture of coarse sand and coarse Perlite.

During a 7-day long period of establishment, seedlings are well-watered and fertilized with $KNO_3$ solution. Thereafter, aqueous solutions of lead in the form of $Pb(NO_3)_2$ or chromium in a form of $K_2Cr_2O_7$ are administered to the surface of the growing medium to obtain 625 ug $Pb^{+2}$ or 3.5 ug $Cr^{+6}$ per gm of dry soil. After the metal application, plants are irrigated with water only. Control plants are watered from the top with $KNO_3$ solution on the day of metal treatment to deliver the same amount of $NO_3^{-1}$ or $K^{+1}$ as the salts of metals. For all treatments the excess soil moisture is trapped in 4 inch plastic saucers placed below each pot. Roots and shoots of treated and control plants are harvested 12 to 20 days after the metal treatment. Metal content, dry matter accumulation, and metal-related toxicity in treated plants is determined and compared to the untreated control. Metal content of roots and shoots is measured by direct current plasma spectrometry.

In an interspecies screen summarized below, lead uptake by members of the Brassiceae tribe (*) was compared with non-Brassica plants and with each other (Table 1).

TABLE 1

Lead-accumulating capacities of different members of Brassiceae tribe (*). The experiment was repeated with similar results. Standard error did not exceed 30% of the mean. Lead content (ug $Pb^{+2}$/g dry weight).

| Plant | Tissue | Days after treatment | |
| --- | --- | --- | --- |
| | | 12 | 20 |
| B. juncea * | Shoot | 9,346 | 18,812 |
| | Root | 70,090 | 91,666 |
| B. carinata * | Shoot | 1,856 | 8,757 |
| | Root | 76,815 | 115,461 |
| B. nigra * | Shoot | 1,439 | 2,489 |
| | Root | 29,671 | 110,011 |
| B. campestris * | Shoot | 1,242 | 6,941 |
| | Root | 22,651 | 100,354 |
| B. oleracea * | Shoot | 2,333 | 1,416 |
| | Root | 51,420 | 51,399 |
| B. napus * | Shoot | 5,720 | 3,877 |
| | Root | 68,117 | 60,768 |
| Sinapis arvensis * | Shoot | — | 498 |
| | Root | — | 42,660 |
| Raphanus sativus * | Shoot | — | 886 |
| | Root | — | 44,157 |
| Nicotiana tabacum | Shoot | — | 786 |
| | Root | — | 24,872 |
| Sorghum bicolor | Shoot | — | 280 |
| | Root | — | 14,693 |
| Zea mays | Shoot | — | 236 |
| | Root | — | 8,165 |

Of all the species studied, Brassica juncea was the best accumulator of lead in shoots, accumulating lead 30-fold over soil values. B. carinata accumulated the highest levels of lead in roots, accumulating lead about 185-fold over soil values. In general, all species of brassicas accumulated exceptionally high levels of lead in shoots and roots. Other members of the Brassiceae tribe were also good accumulators of lead when compared to species belonging to different taxonomic groups. Over ninety percent of lead present in the shoots of B. juncea grown on lead-containing medium for 12 days was present in the stems and reproductive tissue. Leaves contained smaller amounts of lead on a dry weight basis.

In addition to having the highest accumulating ability in the shoot portions, B. juncea showed low lead toxicity. It is also known to be a high biomass producer (average yield of 18 tons/hectare: See, Bhargava, S. C., "Physiology", pp. 161–197 in Oilseed brassicas in Indian Agriculture, (eds. Chopra, V. L. and Prakashs, S.), Vikas Publishing House Ltd, New Delhi, (1991)).

EXAMPLE 3

EMS Mutagenesis

This example illustrates a protocol for use in mutagenizing plant members of the family Brassicaceae.

1. Dry seeds are placed in about 100 ml of a 0.3% (v/v) solution of EMS (obtained from Sigma chemicals, St. Louis, Mo.). There may be some variation from batch to batch of EMS so it may be necessary to adjust this concentration somewhat. Between 20,000 to 250,000 seeds are mutagenized at a time. Ethyl methane sulfonate (EMS) is a volatile mutagen. It should be handled only in a fume hood and all solutions and materials which it contacts should be properly disposed of.

2. Seeds are mixed occasionally or stirred on a stir plate and left at room temperature for 16–20 hours. The rate of mutagenesis may be temperature-dependent so using a magnetic stir plate may alter the results by warming the solution.

3. Seeds are washed with distilled water 10 to 15 times over the course of 2 to 3 hours by decanting the solution, adding fresh water, mixing, allowing the seeds to settle, and decanting again. After about 8 washes the seeds are transferred to a new container and the original is disposed of.

4. After washing, the seeds are immediately sown at about 1 seed per square cm (3000 seeds in 50 ml of 0.1% agar per 35×28×9 cm flat).

5. After several weeks it is useful to estimate the number of seeds which have germinated in order to know the size of the M1 generation. About 75% of the mutagenized seeds usually germinate. Ideally, the M1 estimate is the number of plants which produce M2 seed, but this is much more difficult to measure.

6. Plants are grown until they begin to die naturally and are then allowed to dry completely before harvesting. Complete drying improves the yield and simplifies harvesting.

EXAMPLE 4

Selection of Brassica Cultivars

Identification of *B. juncea* as the best shoot accumulator (see Example 1) allowed an exhaustive screening of 120 *B. juncea* cultivars hoping to utilize existing genetic variability and find the best metal-extracting cultivars. *B. juncea* cultivars originating from 4 different continents were obtained from Dr. Peter K. Bretting, USDA/ARS, Iowa State University, Ames, Iowa 50011. The screening methods described in Example 1 were used throughout. Seedlings were exposed to 625 micrograms lead per gram dry weight soil for 14 days.

Figure 1A:
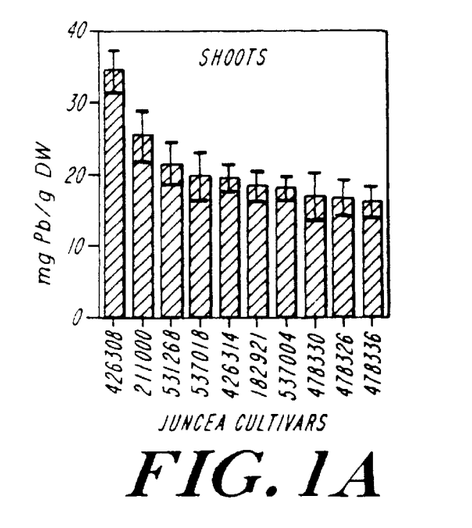
Figure 1B:
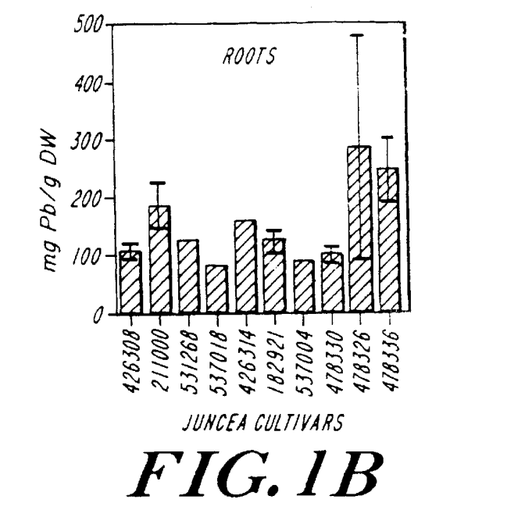

FIG. 1 demonstrates the ability of the ten best lead-accumulating cultivars of *B. juncea* identified in our screen to concentrate lead in shoots (A) and roots (B). Cultivar 426308, the best shoot accumulator identified so far, accumulated almost 55-fold lead in the dried shoots, a lead concentration of 3.5%. Moreover, roots of 426308 were able to concentrate lead 173-fold over the lead levels in the growing medium. This is equivalent to about 10% by weight of lead in the dried roots. The highest root accumulation was, however, observed in lines 211000, 478326 and 478336. These cultivars concentrated lead in their roots about 320-fold, 480-fold, and 350-fold, respectively, equivalent to about 20%, 30% and 25% by weight of lead in the dried roots. All lead-accumulating cultivars are vigorous plants with high biomass production—another important trait for a plant to be used for metal extraction.

In chemical engineering terms, *Brassica juncea* roots can perform chemical precipation and are an extremely effective ion exchange resin and stabilize lead in the soil, as demonstrated below. Twelve day old seedlings of *Brassica juncea* cultivar 173874 are transplanted in groups of 15 plants each into 3.5" pots with a sand/Perlite mixture (150 g/pot by dry wt.), placed in 4.5" plastic saucers, and allowed to grow further for 20 days. At the same time, pots containing the same amounts of sand-Perlite mixtures but without plants are maintained as controls. Each pot (with and without plants) is watered on alternate days with 100 mL of tap water. In addition, 30 milliliters of full strength Hoagland nutrient solution are added weekly to each pot. At the end of the 20th day after transplanting, pots with and without plants are flushed with 10 volumes of tap water. Thereafter, the lead solution is administered into each pot to obtain the final lead concentration of 625 ppm in dry soil. Control pots and pots with plants are watered with tap water every other day.

Figure 2:
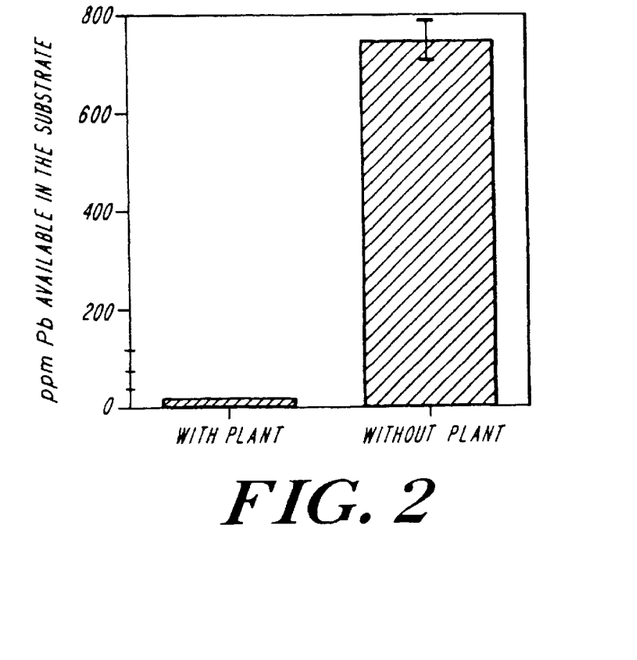
FIG. 2 is a bar graph illustrating stabilization of lead by *B. juncea*.

On the sixth day after lead treatment, 1 ml of solution leached from each pot into the plastic saucer is collected to determine the available lead by atomic absorption spectroscopy. As shown in FIG. 2, in the pots without plants, between about 700–800 ppm lead was measured in the leachate. In the pots with plants, less than 20 ppm lead was measured. The experiment indicates that *B. juncea* roots can effectively make lead much more difficult to leach from the soil.

EXAMPLE 5

Accumulation of Chromium.

Chromium is much more toxic to plants than lead. Eighteen micrograms $Cr^{+6}$/g DW soil, supplied for 20 days, were lethal for all tested Brassica species. Lethality is determined by observations of plant wilting and death by the end of the treatment. Tissue chromium is measured by plasma spectrometry following ashing and acid extraction. See Soltanpour et al, supra. However, at lower concentrations of $Cr^{+6}$ (about 3 to about 9 micrograms $Cr^{+6}$/g soil), crop-related brassicas are extremely good accumulators of this metal. In particular, both *B. juncea* and *B. oleracea* are excellent accumulators of $Cr^{+6}$ (Table 2). For example, *B. juncea* cultivar 21100 concentrated chromium in its roots 650-fold and in its shoots 90-fold. Therefore, the accumulating capacity for chromium in both shoots and roots of Brassicaceae species is even higher than for lead. *B. juncea* is likely better suited for chromium remediation than *B. olercea* because of its higher biomass production and ease of cultivation. To our knowledge, the above experiments are the first conclusive demonstration of the ability of any plant to accumulate chromium.

TABLE 2

Phytoremediation capacities of *B. oleracea* and *B. juncea* exposed to 3.5 and 8.5 μg $Cr^{+6}$/g dry soil for 20 d. Chromium content is expressed as microgram total $Cr^{+6}$/g dry weight tissue.

|  |  | μg $Cr^{+6}$/g tissue |  |
| --- | --- | --- | --- |
| Plant | Tissue | 3.5 | 8.5 |
| *B. oleracea* | Shoot | — | 3 ± 53 |
|  | Root | — | 2578 ± 204 |
| *B. juncea* cultivars: |  |  |  |
| Rcb J* | Shoot | — | 398 ± 43 |
|  | Root | — | 1705 ± 136 |

TABLE 2-continued

Phytoremediation capacities of *B. oleracea* and *B. juncea* exposed to 3.5 and 8.5 µg $Cr^{+6}$/g dry soil for 20 d. Chromium content is expressed as microgram total $Cr^{+6}$/g dry weight tissue.

| Plant | Tissue | µg $Cr^{+6}$/g tissue 3.5 | 8.5 |
|---|---|---|---|
| 182921 | Shoot | 226 ± 64 | — |
| | Root | 1834 ± 35 | |
| 211000 | Shoot | 334 ± 112 | — |
| | Root | 2265 ± 239 | |
| 173874 | Shoot | 182 ± 81 | — |
| | Root | 1945 ± 7 | |

*Rcb J- obtained from Crucifer Genetics Cooperative, Madison, WI.

EXAMPLE 6

Accumulation of Other Heavy Metals

Figure 3:
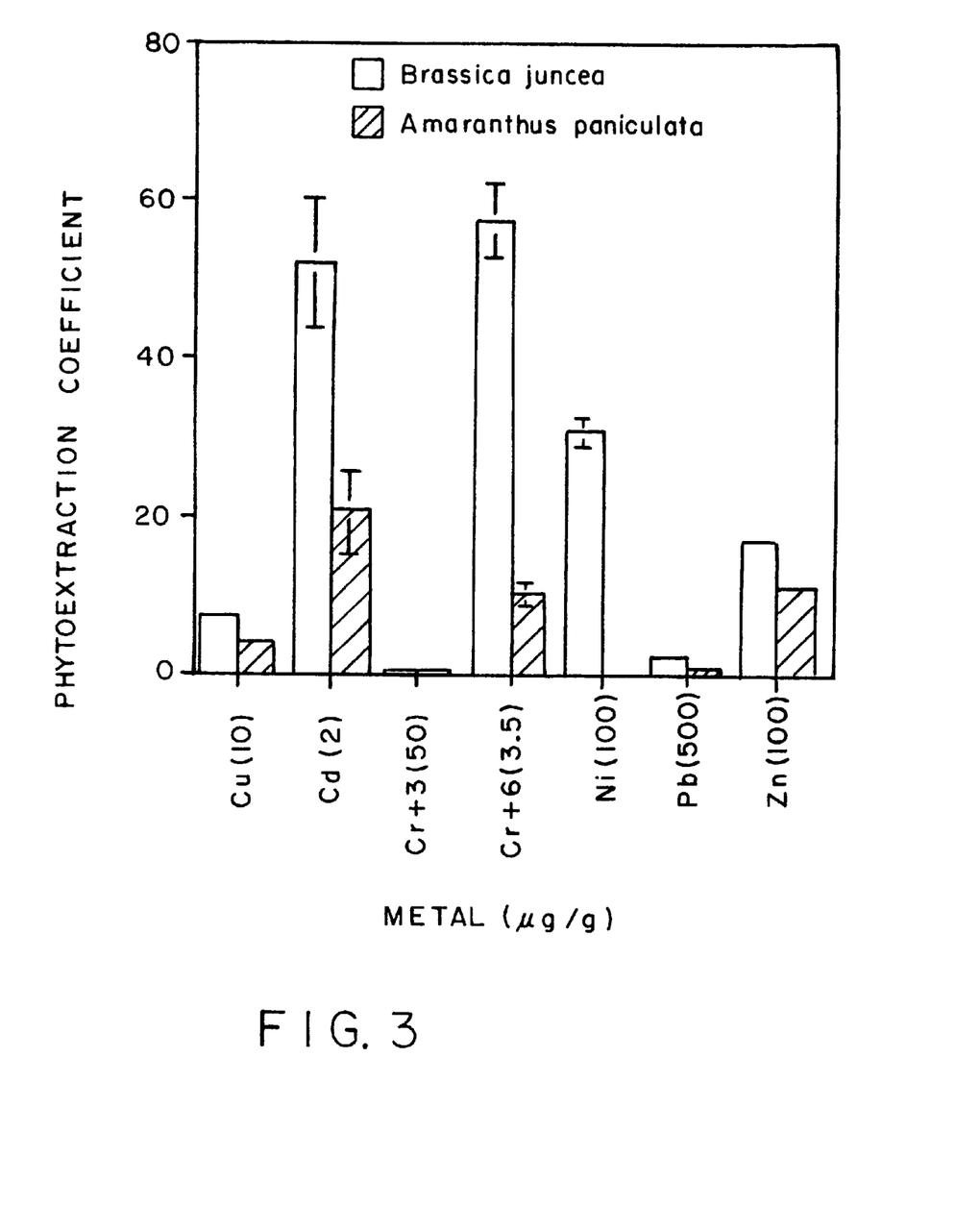
FIG. 3 is a bar graph illustrating accumulation of various metals by *B. juncea* and *A. paniculata*. Levels of metal applied (microgram metal/gram soil) are shown in parenthesis next to the metal symbol. "Phytoextraction coefficient" is the ratio of metal concentration in root tissue (dry weight basis) to metal concentration in soil (dry weight basis).

Seedlings of *Brassica juncea* and *Amaranthus paniculata* are grown in 3.5" pots with a sand/Perlite mixture (150 g/pot by dry wt.), placed in 4.5" plastic saucers, and allowed to grow for 21 days at which point solutions of different metals were added to the soil. Between 2–500 micrograms of metal/gram soil were applied. Each pot is watered on alternate days with 100 mL of tap water. In addition, 30 milliliters of full strength Hoagland nutrient solution are added weekly to each pot. Metal concentration in roots and in soil is measured 14 days after addition of metals. A metal accumulation potential is calculated by dividing metal concentration in root tissue on a dry weight basis to metal concentration in soil, on a dry weight basis. FIG. 3 illustrates that both plants will accumulate cadmium, chromate and zinc, but that *B. juncea* will accumulate nickel as well.

EXAMPLE 7

Vector Construction and Transformation of *B. juncea* with MT Genes

A. Vector Construction

Monkey MT cDNAs (MT1 & MT2) are obtained from Dr. Dean H. Hamer, National Institutes of Health, Bethesda, Md. A 341 bp Hind III/Bam HI fragment containing the entire MT1 coding sequence including the initiator methionine codon is cloned into the Hind III/Bgl II site of pJB90 to give plasmid pNK1. pJB90, a derivative of pGSFR780A (a gift from Dr. Deepak Pental, Tata Energy Research Institute, New Delhi, India) is an Agrobacterium based binary, plant transformation/expression vector. This plasmid contains a plant selectable hpt (hygromycin phosphotransferase) gene and a multiple cloning site for the insertion of foreign DNA, between the T-DNA border repeats. The plasmid also contains a gene for spectinomycin resistance, functional in bacterial cells. pNK1 propagated in *E. coli* Dh5 was used to transform *Agrobacterium tumefaciens* strain pGV2260 (Deblaere et al., *Nucl- Acids Res.*, 13:4777 1985) by the freeze-thaw method (Ebert et al., *PNAS, U.S.A.*, 84:5745 1987).

B. Transformation of *B. juncea*

The 10 best hyperaccumulating *B. juncea* lines—173874, 182921, 211000, 250133, 426314, 426308, 531268, 537004, 537018—were selected for transformation.

*Agrobacterium tumefaciens* strain pGV2260 carrying pNK1 is grown overnight (220 rpm, 28° C. in dark) in 5 mL of liquid YEB (0.5% beef extract; 0.1% yeast extract; 0.5% peptone; 0.5% sucrose; 0.005% $MgSO_4.7H_2O$ in distilled water) containing 100 mg/L each of spectinomycin and rifampicin. One mL of this suspension is used to inoculate 50 mL of the YEB with the same concentrations of antibiotics and allowed to grow overnight. On the third day, the bacteria are harvested by centrifugation (5500 rpm) and resuspended in filter sterilized liquid MS (see Murashige, T., and Skoog, F., *Physiol. Plant*, 15: 473–497 (1962)) modified medium (MS salts & vitamins with 10 g/L each of sucrose, glucose and mannitol) supplemented with 200 micromolar acetosyringone and 100 mg/L each of spectinomycin and rifampicin at pH 5.6. The optical density of the bacterial suspension is adjusted to about $A_{600}=1.0$ and the bacteria grown for 6 hours, harvested as before are resuspended in the same medium. Freshly cut hypocotyl explants are incubated in the bacterial suspension for 1 h and co-cultivated on MS modified medium supplemented with 2 mg/L BAP (6-benzylaminopurine) and 0.1 mg/L NAA (naphthaleneacetic acid). After 2 days the explants are transferred to MS medium supplemented with 2 mg/L BAP, 0.1 mg/L 2,4-D (2-4 dichlorophenoxyacetic acid), 200 mg/L Cefotaxime and 30 micromolar $Ag(NO_3)_2$ and 10 mg/L Hygromycin B. After 10 days incubation on this medium, the explants are shifted to MS supplemented with 2mg/LBAP, 0.1 mg/L NAA, 200 mg/L Cefotaxime, 10 mg/L Hygromycin B and 10% coconut milk. Shoots developed in 15–20 days are grown further and rooted in the presence of 20 mg/L hygromycin. We have obtained transformants with the line 173874 at a frequency of about 2%.

C. Characterization of MT Gene Expression in Transgenic Plant Lines

About 15 independent transgenic plants are generated for each *B. juncea* line mentioned above. The putative transformants are analyzed for the presence of MT1 DNA by Southern and Northern hybridization analysis using MT1 cDNA as a probe. The putative transformants are analyzed for expression of MT1 protein by immunoblot analysis with antisera against monkey MT.

Transgenic lines expressing high MT levels are selected and tested for lead and chromium accumulation and metal tolerance in greenhouse trials described above. The transgenic lines are evaluated in large scale greenhouse trials which will utilize lead and chromium contaminated soil collected from the polluted sites.

CONCLUSIONS

The plant members described in the present invention represent a dramatic improvement in the ability to accumulate metals because of their much higher total biomass accumulation than wild, non-crop-related members of the Brassicaceae described in the literature. For example, *B. juncea* on an average yields 18 tons/hectare of harvestable biomass (Bhargava, S. C., supra). This is an order of magnitude higher than can be expected from the wild, non crop-related species of the Brassicaceae grown under the most favorable conditions.

Based on the available information, the following calculation of the rate of lead removal from contaminated soils can be made. Assuming total above-ground biomass production of 10 tons/hectare and 3.5% (dry weight) lead accumulation in plant shoots, one planting of the best lead-accumulating lines of *Brassica juncea* (cultivar 426308) can remove as much as 350 kg lead/hectare. In most of the areas of the United States, 3 sequential crops of this plant can be grown each year. Therefore, the best metal-accumulating lines of crop brassicas selected according to the methods of the present invention can extract one ton of lead per hectare per year. These estimates of the metal-removing capabilities of crop-related plants of the present invention assume that the soils can be extracted to a depth of up to one meter, which approximates the depth to which the roots of crop-related members of the family Brassicaceae can reach under favorable conditions.

The most commonly used method for cleaning toxic metal-contaminated soil is removal and isolation which costs an average of about $400 per ton of soil. If the contamination is 80 cm deep in sandy loam soil having a density of about 2.0 grams/cm., it will cost about $2.56 million to clean up one acre using this soil removal method.

The cost of growing the crop-related members of the Family Brassicaceae in the present invention may be approximated from the cost of alfalfa production in New Jersey which is about $320.00 per acre for the average farmer. Approximately 4.2 tons of dry plant matter per acre can be reduced to 40 kilograms of ash per acre if the plants are incinerated. Removing and burying that much plant residue will cost from about $640 to about $1,680 per acre, making the total cost of one crop between $960 and $2,000. Therefore, growing even ten sequential crops of the plants described in the present invention will be several orders of magnitude cheaper than a soil removal method. Furthermore, this method is better for the environment since it reclaims the soil making it usable rather than permanently disposing of the soil.

Under some circumstances, the metal can actually be reclaimed from the highly enriched plant ash. This will completely eliminate the need for residue burial and provide a truly environmentally friendly remediation technology.

EQUIVALENTS

It should be understood that various changes and modifications of the preferred embodiments may be made within the scope of the invention. Thus it is intended that all matter contained in the above description be interpreted in an illustrative and not limited sense.

What is claimed is:

1. A method of removing an amount of a metal from a soil environment, comprising:
    identifying a soil environment containing a metal selected from the group consisting of antimony, arsenic, barium, beryllium, cadmium, chromium, cobalt, copper, gold, lead, manganese, molybdenum, nickel, palladium, selenium, silver, strontium, tin, vanadium, and zinc;
    planting at least one plant in said soil environment;
    manipulating said soil environment by adding an effective amount of an appropriate chelating agent to said soil environment, so that a soluble complex is formed between said metal and said chelating agent, said effective amount of chelating agent being an amount sufficient to increase availability of said metal to said plant to the extent that said plant can accumulate said metal to a concentration higher than the concentration of said metal in said soil environment; and
    maintaining said plant in said manipulated soil environment under conditions and for a time sufficient for said plant to accumulate said metal from said manipulated soil environment, so that the concentration of accumulated metal in said plant is higher than the concentration of said metal in said environment.

2. The method of claim 1, where the metal is selected from the group consisting of chromium, manganese, selenium, and zinc.

3. The method of claim 1, where the soil environment contains at least two metals selected from the group consisting of antimony, arsenic, barium, beryllium, cadmium, chromium, cobalt, copper, gold, lead, manganese, molybdenum, nickel, palladium, selenium, silver, strontium, tin, uranium, vanadium, and zinc.

4. A method of removing an amount of uranium from a soil environment, comprising:
    identifying a soil environment containing uranium;
    planting at least one plant in said soil environment;
    manipulating said soil environment by adding an effective amount of an appropriate chelating agent to said soil environment, so that a soluble complex is formed between said uranium and said chelating agent, said effective amount of chelating agent being an amount sufficient to increase availability of said uranium to said plant to the extent that said plant can accumulate said uranium to a concentration higher than the concentration of said uranium in said soil environment; and
    maintaining said plant in said manipulated soil environment under conditions and for a time sufficient for said plant to accumulate said uranium from said manipulated soil environment, so that the concentration of accumulated uranium in said plant is higher than the concentration of said uranium in said environment.

5. A method of removing an amount of a metal from a soil environment, comprising:
    identifying a soil environment containing a metal toxic to plants;
    planting at least one plant in said soil environment;
    manipulating said soil environment by adding an effective amount of an appropriate chelating agent to said soil environment, so that a soluble complex is formed between said metal and said chelating agent, said effective amount of chelating agent being an amount sufficient to increase availability of said metal to said plant to the extent that said plant can accumulate said metal to a concentration higher than the concentration of said metal in said soil environment; and
    maintaining said plant in said manipulated soil environment under conditions and for a time sufficient for said plant to accumulate said metal from said manipulated soil environment, so that the concentration of accumulated metal in said plant is higher than the concentration of said metal in said environment.

6. The method of claim 1, 4, or 5 wherein the step of manipulating comprises applying an amount of an acid to the soil environment, the amount being sufficient to adjust pH of the soil environment to below pH 5.0.

7. The method of claim 6, where the acid is an organic acid selected from the group consisting of acetic acid and citric acid.

8. The method of claim 1, 4, or 5 wherein the step of manipulating comprises adding an effective amount of chelating agent selected from the group consisting of ammonium purpurate (murexide), 2,3-butane-dione dioxime (dimethylglyoxime), 3,6 disulfo-1,8-dihydroxynaphthalene (chromotroic acid), thiourea, alpha-benzoin oxime (cupron), trans-1,2-diaminocyclohexanetetraacetic acid (CDTA), diethylene-triaminopentaacetic acid (DTPA), 2,3-dimercapto-1-propanol, diphenylthiocarbazone, nitrilotriacetic acid (NTA), substituted 1,10-phenanthrolines, sodium deithyldithiocarbamate (cupral), 2-thenoyl-2- furoylmethane, thenoyl-trifluoroacetone, triethylenetetramine, ethylenediaminetetraacetic acid (EDTA) and citric acid.

9. The method of claim 1 or 5, wherein the step of maintaining comprises maintaining said plant in said manipulated soil environment under conditions and for a time sufficient for said plant to accumulate a total of at least about 1% of its shoots on a dry weight basis as metal.

* * * * *